(12) United States Patent
Froom et al.

(10) Patent No.: US 6,187,949 B1
(45) Date of Patent: Feb. 13, 2001

(54) SYNTHESIS OF LOWER ALIPHATIC ESTERS USING HETERPOLYACIDS WITH AN ALDEHYDE-FREE PRODUCT STREAM

(75) Inventors: Simon Frederick Thomas Froom; Stephen Robert Hodge, both of East Yorkshire; Bhushan Sharma, Surrey, all of (GB)

(73) Assignee: BP Chemicals Limited, London (GB)

( * ) Notice: Under 35 U.S.C. 154(b), the term of this patent shall be extended for 0 days.

(21) Appl. No.: 09/235,274

(22) Filed: Jan. 22, 1999

(30) Foreign Application Priority Data

Jan. 22, 1998 (GB) .................................................. 9801426
Aug. 12, 1998 (GB) .................................................. 9817571

(51) Int. Cl.$^7$ .................................................. C07C 67/04
(52) U.S. Cl. .................................................. 560/247
(58) Field of Search .................................................. 560/247

(56) References Cited

U.S. PATENT DOCUMENTS 5,189,201  2/1993  Sano et al. .
5,861,530 * 1/1999  Atrkins et al. .

FOREIGN PATENT DOCUMENTS 0 562 139 A1  9/1993  (EP) .
0 757 027 A1  2/1997  (EP) .
1259390       1/1972  (GB) .

* cited by examiner

Primary Examiner—James O. Wilson
Assistant Examiner—Robert W. Deemie
(74) Attorney, Agent, or Firm—Nixon & Vanderhye

(57) ABSTRACT

Process for the production of lower aliphatic esters by bringing together in an addition reaction a lower olefin and a saturated, lower aliphatic, mono-carboxylic acid in the vapor phase into contact with a heterpolyacid catalyst. The reactant olefin and acids and any recycled feeds are rendered substantially free of aldehydes impurities prior to being brought into contact with the heterpolyacid catalyst. Acetaldehyde is a catalyst poison and removal of these from the feeds prolongs life and activity of the heteropolyacid catalyst.

18 Claims, No Drawings

SYNTHESIS OF LOWER ALIPHATIC ESTERS USING HETERPOLYACIDS WITH AN ALDEHYDE-FREE PRODUCT STREAM

The present invention relates to a process for the synthesis of esters by reacting an olefin with a lower carboxylic acid in the presence of an acidic catalyst.

It is well known that olefins can be reacted with lower aliphatic carboxylic acids to form the corresponding esters. One such method is described in GB-A-1259390 in which an ethylenically unsaturated compound is contacted with a liquid medium comprising a carboxylic acid and a free heteropolyacid of molybdenum or tungsten. This process is a homogeneous process in which the heteropolyacid catalyst is unsupported. A further process for producing esters is described in JP-A-05294894 in which a lower fatty acid is esterified with a lower olefin to form a lower fatty acid ester. In this document, the reaction is carried out in the gaseous phase in the presence of a catalyst consisting of at least one heteropolyacid salt of a metal eg Li, Cu, Mg or K, being supported on a carrier. The heteropolyacid used is phosphotungstic acid and the carrier described is silica. One of the problems with this process is that impurities present in the feeds to the reaction whether they be fresh feeds or recycle streams from the process have a tendency to deactivate the acid catalyst. In particular, presence of an aldehyde such as acetaldehyde in amounts at or above 100 ppm in the feed streams are detrimental to the heteropolyacid catalyst.

It has now been found that the process efficiency can be improved significantly by using a gaseous feedstock substantially free of such impurities.

Accordingly the present invention is a process for the production of lower aliphatic esters by bringing together in an addition reaction reactants comprising a lower olefin and a saturated, lower aliphatic, mono-carboxylic acid in the vapour phase into contact with a heteropolyacid catalyst characterised in that the reactants are rendered substantially free of aldehydes impurities prior to being brought into contact with the heteropolyacid catalyst.

By the expression "substantially free of aldehyde impurities is meant here and throughout the specification that the reactants comprise (a) a feedstream (comprising the lower olefin, and a saturated, lower aliphatic, mono-carboxylic acid, and optionally water, which feed stream may optionally contain any ether or alcohol recycled to the feedstream) to the reactor, and (b) contain less than 90 ppm, preferably less than 60 ppm and more preferably less than 55 ppm of aldehyde impurities prior to the feedstream entering the reactor inlet.

The aldehyde impurities in particular are detrimental to the acid catalyst and cause deactivation. A particular example of such an impurity is acetaldehyde. Such impurities may either be present in the fresh feeds to the reaction or may be formed as a by-product in the reactors during reaction and tend to be recycled to the reactor along with light products such as diethyl ether and if not checked quickly, tend to build up to levels far in excess of the tolerance levels specified above.

The aldehyde impurities are believed to cause deactivation of the heteropolyacid catalyst by reaction to form "coke" or unwanted resinification due to oligomerisation which then tend to block the catalyst pores. Whilst this is believed to be one of the mechanisms of such deactivation, it is by no means the only mechanism. The feedstream to the reaction is rendered free of any aldehyde impurities by subjecting the feedstream to a technique selected from:

a. distillation,
b. reaction with an solution of a base such as eg sodium hydroxide,
c. reaction with a borohydride such as eg sodium borohydride,
d. reaction with an acidic or a basic resin, and
e. extraction eg with acid or water.

Of these, distillation is the easiest and most convenient technique, especially to remove any aldehydes contained the ether by-products being recycled. Such distillation is suitably performed in a pressurised column.

The reaction with a base or a borohydride may also be suitably carried out in a distillation column or in a separate vessel. Where a resin is used, the feedstream which may be in the liquid or gas phase, is suitably brought into contact with the acidic or the basic resin.

In the reaction, the olefin reactant used is suitably ethylene, propylene or mixtures thereof Where a mixture of olefins is used, the resultant product will inevitably be a mixture of esters. The mixture of olefins is suitably sourced from a refinery product or a chemical grade olefin which also contains some alkanes admixed therewith.

The saturated, lower aliphatic mono-carboxylic acid reactant is suitably a C1–C4 carboxylic acid and is preferably acetic acid.

The reaction may be carried out in a plurality of reactors set up in series such that gaseous products exiting from a first reactor are fed as a feed (reactant) gas to a second reactor and the gaseous products exiting from the second reactor are fed as a feed gas to the third reactor so on for subsequent reactors, and an aliquot of the reactant monocarboxylic acid is introduced into the feed gas to the second and subsequent reactors so as to maintain the olefin to monocarboxylic acid ratio in the feed gas to each of the second and subsequent reactors within a pre-determined range.

Thus, the mole ratio of olefin to the lower monocarboxylic acid in the gaseous reactants fed to the first reactor is suitably in the range from 1:1 to 18:1, preferably from 10:1 to 14:1. During the reaction, when the gaseous reactants come into contact with the heteropolyacid in a catalyst bed, at least some of the acid is used up to form the ester in an exothermic reaction and the mole ratio of olefin to monocarboxylic acid increases considerably from a starting ratio of 12:1 to about 30:1 in the exit gases from the final reactor. Where the reaction is carried out in a plurality of reactors set up in series, the exit gases from the first reactor are fed as the feed (reactant) gas to the second reactor and the exit gases from the second reactor are fed as the feed gas to the third reactor and so on. When using such a series of reactors, the olefin to monocarboxylic acid mole ratio in the feed gas to the second and subsequent reactors is seriously depleted due to the acid being used up in the formation of the ester. This mole ratio of olefin to monocarboxylic acid is brought to the desired range by injecting further aliquots of the monocarboxylic acid to the feed gas prior to its entry into each of the second and subsequent reactors. In the case of the manufacture of ethyl acetate from ethylene and acetic acid, this range of mole ratios of ethylene to acetic acid in the gaseous reactants fed to the first reactor is suitably in the range from 1:1 to 18:1, preferably from 10:1 to 14:1 and that of the feed gas to the second and subsequent reactors is suitably from 10:1 to 16:1. The addition of further aliquots of the monocarboxylic acid to the feed gas to the second and subsequent reactors should be sufficient to bring the mole ratio of the olefin to acid within this range of 10:1 to 16:1.

The plurality of reactors set up in series referred to above can each be disposed in an axial mode with the feed (reactant) and product gases traversing a substantially axial path within each reactor from entering the top of the reactor until the product gases leave each reactor from the base thereof, the catalyst being positioned somewhere midway between the point of entry of the feed gas and the point of exit of the product gases. However, the reactors need not be set-up in a series where the flow-path of the feed (reactant) and product gases are in a substantially axial direction within each reactor. They could be set-up as a series of radial flow reactors. In such a radial flow set-up, the feed (reactant) gases will enter at the top of a reactor, pass down the middle thereof and then outwards radially over the catalyst in said reactor.

Briefly, each radial flow reactor in the series is of a substantially tubular shape which in a planar view has the appearance of a set of three substantially concentric tubes and wherein the feed gases enter from the top into the inner most tube and flow substantially radially outward into a middle annular tube housing the catalyst bed and then, after the addition reaction has taken place over the catalyst bed to generate a gaseous stream of product gases comprising ethyl acetate and the unreacted feed gases, said gaseous stream emerging from the annulus comprising the catalyst bed flows further radially into the outermost tube of said concentric tubular reactor to be fed as feed gas into a second such radial flow reactor; and similarly the product gases exiting from the second reactor are used as feed gas for the third reactor in series and so on. The reactant acid is introduced into the gaseous products stream emergent from each of (a) the first reactor to maintain the desired reactant concentrations in said gaseous products stream so as to enable said stream to be used as the feed gas for the second and (b) the second reactor which is fed as the feed gas to the third reactor and so on to each of the subsequent reactors along in the series. The process can thus be operated by setting up a series of such radial flow reactors. One of the features of the radial flow reactors is that the pressure drop across such a reactor is much less when compared with a series of reactors set-up to operate in a mode where the feed gases and the product gases traverse a substantially vertical path within each reactor. Moreover, the velocity of the reactant (feed) gases over the catalyst bed is also comparatively lower, thereby minimising risk of damage to the catalyst due to attrition. When using radial reactors, there is a possibility that the catalyst bed settles or contracts within the annulus in which the catalyst bed is located creating a void space above the settled catalyst bed through which space the reactant gases may pass without making the desired contact with the catalyst. The risk of this happening may be averted by storing eg a volume of catalyst behind a screen located above the actual bed so that as the catalyst bed itself settles or contracts, a further aliquot of the catalyst is released from behind the screen to fill the voided space above the catalyst thereby minimising loss of the desired contact with the catalyst.

The plurality of reactors need not be a discrete set of individual reactors. The process of the present invention should also work equally effectively if the reaction is carried out in one long reactor which has a plurality of catalyst beds set up in series spaced along the length thereof and the acid is injected into the product gases exiting from the first bed to maintain the range of olefin to monocarboxylic acid within the predetermined range in the second and subsequent beds. In a typical addition reaction it is desirable to use about four reactors set up in series although this can be reduced or increased without adversely affecting the beneficial effect of the injection of the monocarboxylic acid to the feed gas to the second and subsequent catalyst beds or reactors.

The addition reaction is suitably carried out in one or more reactors run under adiabatic conditions. Due to the exothermic nature of the addition reaction, it may be necessary to cool the feed gases to the second and subsequent reactors so as to maintain the reaction temperature within the desired range. This cooling and thus the adiabatic conditions may be achieved, where necessary, either by inserting an intermediate cooling step between the (a) the catalyst beds in a reactor or (b) each of the reactors depending upon whether a single reactor is used with a series of catalyst beds or a series of separate reactors are used. The cooling step is suitably achieved by using one or more of:
   (a) heat exchanger tubes
   (b) injection of
      (i) additional monocarboxylic acid reactant and/or
      (ii) water
      into the feed gases to the second and subsequent reactors.

Whichever set up of reactors is used, the process of the present invention can be improved further by the addition of water as a component of the reaction mixture. The water added to the reaction mixture is suitably present in the form of steam and is capable of generating a mixture of esters and alcohols in the process. It has been found that the presence of water in the reaction mixture in an amount of 1–10 mole %, preferably from 3 to 7 mole %, eg 5 to 6.5 mole %, based on the total moles of reactant acid, olefin and water, enhances the stability of the catalyst and thereby enhances the efficiency of the process. Furthermore, the presence of water also reduces the selectivity of the process to undesired by-products such as eg oligomers and other unknowns, excluding diethyl ether and ethanol. Water addition may also be used to supplement the cooling of the feed gases to the second and subsequent reactors as described above.

It has further been found that dosing the reaction mixture with amounts of a di-ether such as eg diethyl ether, as a co-feed also reduces the formation of undesirable by-products. The amount of di-ether co-fed is suitably in the range from 0.1 to 6 mole %, preferably in the range from 0.1 to 3 mole % based on the total of the olefin, the aliphatic carboxylic acid, water and diethyl ether. The di-ether co-fed may correspond to the by product di-ether from the reaction generated from the reactant olefin. Where a mixture of olefins is used, eg a mixture of ethylene and propylene, the di-ether may in turn be an unsymmetrical di-ether. The di-ether co-feed may thus be the by-product of the reaction which by-product is recycled to the reaction mixture.

The term "heteropolyacid" as used herein and throughout the specification in the context of the catalyst is meant to include the free acids and partial salts thereof. The heteropolyacids used to prepare the esterification catalysts of the present invention therefore include inter alia the free acids and co-ordination type partial acid salts thereof in which the anion is a complex, high molecular weight entity. Typically, the anion comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be used as the catalysts in the present invention include:

12-tungstophosphoric acid—$H_3[PW_{12}O_{40}].xH_2O$
12-molybdophosphoric acid—$H_3[PMo_{12}O_{40}].xH_2O$
12-tungstosilicic acid—$H_4[SiW_{12}O_{40}].xH_2O$
12-molybdosilicic acid—$H_4[SiMo_{12}O_{40}].xH_2O$
Cesium hydrogen tungstosilicate—$Cs_3H[SiW_{12}O_{40}].xH_2O$ The heteropolyacid catalyst whether used as a free acid or as a partial acid salt thereof is suitably supported, preferably on a siliceous support. The siliceous support is suitably in the form of granules, beads, globules, extrudates or pellets.

The siliceous support used can be derived from an amorphous, non-porous synthetic silica especially fumed silica, such as those produced by flame hydrolysis of $SiCl_4$. Specific examples of such siliceous supports include Support 350 made by pelletisation of AEROSIL® 200 (both ex Degussa). This pelletisation procedure is suitably carried out by the process described in U.S. Pat. No. 5,086,031 (see especially the Examples) and is incorporated herein by reference. Such a process of pelletisation or extrusion does not involve any steam treatment steps and the porosity of the support is derived from the interstices formed during the pelletisation or extrusion step of the non-porous silica The silica support is suitably in the form of pellets, granules, beads or are globular in shape having an average particle diameter of 2 to 10 mm, preferably 4 to 6 mm. The siliceous support suitably has a pore volume in the range from 0.3–1.2 ml/g, preferably from 0.6–1.0 ml/g. The support suitably has a crush strength of at least 2 Kg force, suitably at least 5 Kg force, preferably at least 6 Kg and more preferably at least 7 Kg. The crush strengths quoted are based on average of that determined for each set of 50 beads/globules/granules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 Å preferably an average pore radius of 30 to 100 Å.

In order to achieve optimum performance, the siliceous support is suitably free of extraneous metals or elements which might adversely affect the catalytic activity of the system. The siliceous support suitably has at least 99% w/w purity, ie the impurities are less than 1% w/w, preferably less than 0.60% w/w and more preferably less than 0.30% w/w.

Other suitable silica supports are the Grace 57 and 1371 grades of silica. In particular, Grace 57 grade silica has a bulk density of about 0.4 g/ml and a surface area in the range of 250–350 $m^2/g$. Grace silica grade No. 1371 has an average bulk density of about 0.39 g/ml, a surface area of about 500–550 $m^2/g$, an average pore volume of about 1.15 ml/g and an average particle size ranging from about 0.1–3.5 mm. These supports can be used as such or after crushing to an average particle size in the range from 0.5–2 mm and sieving before being used as the support for the heteropolyacid catalyst.

The impregnated support is suitably prepared by dissolving the heteropolyacid, which is preferably a tungstosilicic acid, in eg distilled water, and then adding the support to the aqueous solution so formed. The support is suitably left to soak in the acid solution for a duration of several hours, with periodic manual stirring, after which time it is suitably filtered using a Buchner funnel in order to remove any excess acid.

The wet catalyst thus formed is then suitably dried either by placing in an oven at elevated temperature for several hours or by allowing a heated gas, such as eg nitrogen or air, to flow over the wet catalyst after which it is allowed to cool to ambient temperature in a desiccator. The catalyst loading in g/litre is determined by deducting the weight of the support used from the weight of the catalyst upon drying.

Alternatively, the support may be impregnated with the catalyst using the incipient wetness technique and then dried by flow of a heated gas, such as eg nitrogen or air, over the wet catalyst.

This supported catalyst (measured by weight) can then be used in the process of the invention. The amount of heteropolyacid deposited/impregnated on the support for use in the reaction is suitably in the range from 10 to 60% by weight, preferably from 20 to 50% by weight, more preferably 20–35% by weight (which corresponds to about 100–215 g/litre), based on the total weight of the heteropolyacid and the support.

The reaction is carried out in the vapour phase suitably above the dew point of the reactor contents comprising the reactant acid, any alcohol formed in situ, the product ester and water as stated above. Dew point is the temperature at which condensation of a vapour of a given sample in air takes place. The dew point of any vaporous sample will depend upon its composition. The supported heteropolyacid catalyst is suitably used as a fixed bed in each reactor which may be in the form of a packed column. The vapours of the reactant olefins and acids are passed over the catalyst suitably at a GHSV in the range from 100 to 5000 per hour, preferably from 300 to 2000 per hour.

The reaction is suitably carried out at a temperature in the range from 150–200° C. within which range the entry temperature of the reactant gases is suitably from 160–180° C. and the temperature of the exit gases from each reactor is suitably 170–200° C. The temperature of the catalyst is slowly ramped up as the catalyst deactivates, eg by increasing the temperature of the feed to the first reactor, thereby maintaining productivity. The reaction pressure is suitably at least 400 KPa, preferably from 500–3000 Kpa, more preferably about 1000 Kpa depending upon the relative mole ratios of olefin to acid reactant and the amount of water used.

The products of the reaction are recovered by, for example, fractional distillation. The esters produced, whether singly or as mixture of esters, may be hydrolysed to the corresponding alcohols or mixture of alcohols in relatively high yields and purity.

The process of the present invention is particularly suited to making ethyl acetate from ethylene and acetic acid by an addition reaction with optional recycle of any ethanol or diethyl ether formed.

The present invention is further illustrated with reference to the following Examples and Comparative Tests.

EXAMPLES

In all the Examples, the reaction conditions used and the results achieved are tabulated below. In these tables, the following abbreviations have been used:

| | |
|---|---|
| HOS | Hours on stream |
| Bed (T/M/B) | Bed (top/middle/bottom) |
| HAC | Acetic Acid |
| $C_2H_4$ | Ethylene |
| $H_2O$ | Water |
| EtAc | Ethyl acetate |
| EtOH | Ethanol |
| DEE | Diethyl ether |
| GHSV | Gas hourly space velocity |
| g/Lcat/h | Gram per liter of catalyst per hour |
| STP | Standard temperature & pressure |
| STY | Space time yield |

Example 1

Catalyst Preparation:

Silica pellets (Grace 57 grade, surface area 310 m²/g, bulk density 0.4 g/ml, pore volume 1.03 ml/g, ca. 5–8 mm, 9.3 kg, ex W R Grace) were soaked in a solution of silicotungstic acid [$H_4SiW_{12}O_{40}$] (32 kg of 26% w/w aqueous solution) in order to impregnate the silica support with the silicotungstic acid catalyst. After this duration, excess catalyst solution was drained off. The resultant catalyst impregnated support pellets were then dried using a warm nitrogen stream to give a catalyst with a loading of 140 g/litre.

Catalyst Testing:

Three reactors, designed to simulate an adiabatic operation, were set up in series with intercoolers. The feedstream was heated in a vaporiser and passed into the top of the first reactor at 176° C. and 1000 Kpa pressure. The exit gases from the top reactor were cooled and fed into the second reactor at 172° C. and the exist gases from this second reactor were cooled and fed into a third reactor at 168° C. The exit gases from the third reactor were cooled and passed into a vapour-liquid separator at 30° C. The vapour stream from the separator was compressed and recycled to the vaporiser. The liquid stream from the separator was reduced in pressure to atmospheric and samples were analysed by gas chromatography.

The feed to the first reactor was made up of ethylene (3385 g/hr), acetic acid (616 g/hr), water (152 g/hr), ethanol (40 g/hr), diethyl ether (40 g/hr) and ethyl acetate (92 g/hr) and acetaldehyde defined in amounts recited in the Table below. The three reactors were charged with 329 g, 414 g and 487 g respectively of the silicotungstic acid catalyst specified above.

The STYs achieved are defined in the Table as g of ethyl acetate/litre of catalyst/hour. The acetaldehyde content was analysed by on-line gas chromatography.

| Examples/ Tests | Acetaldehyde added (g/hr) | Total acetaldehyde to first reactor (ppm) | Deactivation rate STY drop/100 hrs |
|---|---|---|---|
| Ex 1 | 0 | 25 | 1.5 |
| CT1 | 0.23 | 101 | 3.2 |
| CT2 | 0.37 | 147 | 5.3 |

CT - indicates a comparative test not according to the invention.

The results from CT1 and CT2 show that if acetaldehyde is added in the amounts shown to simulate full recycle, the rate of catalyst deactivation is unacceptably high. This demonstrates the need to remove aldehydes from the feedstreams to the addition reaction.

Example 2

The liquid stream from the separator as described in Example 1 typically contains around 90 ppm acetaldehyde. This can be removed from the process by distillation.

The bulk of the acetic acid, ethyl acetate, water, ethanol and heavy by-products are separated from the ex-separator liquid stream using two columns The heads product from the second column containing the light materials is fed to an acetaldehyde distillation column containing 10 theoretical stages. The volatile nature of the components present in this stream necessitated the operation of this column under pressure (1 barg) and at a molar reflux ratio of 38:1. The acetaldehyde removal column thus had 10 theoretical stages and under these conditions allowed 98% by weight of the acetaldehyde to be purged from the system as a heads stream from this column which stream also contained a small amount of diethyl ether. The ether loss was estimated to be 9% by weight in this stream. The base stream from the acetaldehyde removal column contained 67% by weight of diethyl ether and the remaining Light Ends impurities.

The composition of the streams from this acetaldehyde removal column was as shown in Table 8 below:

TABLE 8

| Component | Feed | Heads Product | Base Product |
|---|---|---|---|
| | Amounts in % by wt unless otherwise specified | | |
| Acetic Acid | <10 ppm | <10 ppm | <10 ppm |
| Ethylene | 0.47 | 0 | 0 |
| Ethyl acetate | 3.66 | 73.44 | 3.93 |
| Diethyl Ether | 66.98 | 5.07 | 65.5 |
| Water | 6.13 | 0.2 | 6.38 |
| Ethanol | 0.29 | 3.12 | 0.31 |
| Acetaldehyde | 0.62 | 15.60 | 0.01 |
| Light Ends | 22.33 | 0 | 23.81 |
| Medium Ends | 0 | 0 | 0 |
| Heavy Ends | 0 | 0 | 0 |
| Butanes | 0 | 0 | 0 |
| Butenes | 0 | 0 | 0 |
| Total (kg/hr) | 553 | 108 | 516 |

The temperature profile of this acetaldehyde removal column was as shown in Table 9 below:

TABLE 9

| Stage Number | Temperature (° C.) |
|---|---|
| 1 | 52.2 |
| 2 | 54.4 |
| 3 | 56.0 |
| 4 | 57.7 |
| 5 | 58.1 |
| 6 | 58.5 |
| 7 | 58.9 |
| 8 | 59.3 |
| 9 | 59.8 |
| 10 | 60.7 |

In order to avoid a build up of some of the Light Ends such as the methyl pentanes, a purge of 70.5 kg/hr was taken from the base stream before it was returned back to the reactor.

We claim:

1. A process for the production of lower aliphatic esters comprising bringing into contact in an addition reaction reactants comprising a lower olefin and a saturated, lower aliphatic, mono-carboxylic acid in the vapour phase with a heteropolyacid catalyst wherein the reactants are rendered substantially free of aldehydes impurities prior to being brought into contact with the heteropolyacid catalyst.

2. A process according to claim 1 wherein the reactants (a) are a feedstream comprising the lower olefin, a saturated, lower aliphatic, mono-carboxylic acid and optionally water, which feedstream may optionally contain any ether or alcohol recycled from the process to the feedstream, and (b) contain less than 90 ppm of aldehyde impurities prior to the feedstream entering the reactor inlet.

3. A process according to claim 1 wherein the reactants are a feedstream comprising the olefin, a saturated, lower aliphatic, mono-carboxylic acid and optionally water, which may optionally contain any ether or alcohol recycled from the process to the feedstream, and contain less than 60 ppm of aldehyde impurities prior to the feedstream entering the reactor inlet.

4. A process according to any one of the preceding Claims wherein the reactants are rendered free of any aldehyde impurities by subjecting the feedstream to a technique selected from the group consisting of:
   a. distillation,
   b. reaction with a solution of a base,
   c. reaction with a borohydride,
   d. reaction with an acidic or a basic resin, and
   e. extraction.

5. A process according to claim 4 wherein the reactants are rendered free of any aldehyde impurity by bringing the feedstream which is either in the liquid or in the gaseous phase into contact with an acidic or a basic resin.

6. A process according to claim 1 wherein the olefin reactant is ethylene, propylene or mixtures thereof.

7. A process according to claim 1 wherein the olefin reactant is a mixture of olefins sourced from a refinery product or a chemical grade olefin which also contains some alkanes admixed therewith.

8. A process according to claim 1 wherein the saturated, lower aliphatic mono-carboxylic acid reactant is a C1–C4 carboxylic acid.

9. A process according to claim 1 wherein the saturated, lower aliphatic, mono-carboxylic acid is acetic acid.

10. A process according to claim 1 wherein the mole ratio of olefin to the lower monocarboxylic acid in the reactants fed to the first reactor is suitably in the range from 1:1 to 18:1.

11. A process according to claim 10 wherein the mole ratio of olefin to the lower monocarboxylic acid in the reactants fed to the second and subsequent reactors is in the range from 10:1 to 16:1.

12. A process according to claim 1 wherein the reactants comprise a lower olefin, a saturated, aliphatic monocarboxylic acid and water in an amount of 1–10 mole % based on the total moles of reactant acid, olefin and water.

13. A process according to claim 1 wherein the heteropolyacid catalyst is the free heteropolyacid or a partial salt thereof.

14. A process according to claim 1 wherein the heteropolyacid catalyst whether used as a free acid or as a partial acid salt thereof is supported.

15. A process according to claim 14 wherein the support for the heteropolyacid catalyst is a siliceous support.

16. A process according to claim 15 wherein the silica support has an average particle diameter of 2 to 10 mm, a pore volume in the range from 0.3–1.2 ml/g, an average pore radius (prior to use) of 10 to 500 Å and a crush strength of at least 2 Kg force.

17. A process according to claim 1 wherein the addition reaction is carried out at a temperature in the range from 150–200° C. and reaction pressure of at least 400 KPa.

18. A process according to claim 1 wherein ethylene is reacted with acetic acid in the vapour phase in the presence of a heteropolyacid catalyst supported on a siliceous support to form ethyl acetate.

* * * * *